United States Patent [19]
van der Zel

[11] Patent Number: 5,362,438
[45] Date of Patent: Nov. 8, 1994

[54] POWDER OF DENTAL METAL, A PROCESS FOR THE PREPARATION THEREOF, A PROCESS FOR THE MANUFACTURE OF A SUBSTRUCTURE FOR A DENTAL RESTORATION AND A PROCESS FOR THE MANUFACTURE OF A DENTAL RESTORATION

[75] Inventor: Joseph M. van der Zel, Zwaag, Netherlands

[73] Assignee: Elephant Edelmetaal B.V., Hoorn, Netherlands

[21] Appl. No.: 74,448

[22] Filed: Jun. 10, 1993

Related U.S. Application Data

[62] Division of Ser. No. 660,020, Feb. 25, 1991, Pat. No. 5,238,751.

[51] Int. Cl.$^5$ .................... B22F 5/00; B22F 7/00; A61C 13/08
[52] U.S. Cl. .................... 419/28; 419/35; 419/47; 433/207; 433/208
[58] Field of Search ............ 419/28, 35, 47; 433/207, 202

[56] References Cited

U.S. PATENT DOCUMENTS

| | | | |
|---|---|---|---|
| 3,502,466 | 3/1970 | Vickery | 75/208 |
| 4,011,077 | 3/1977 | Kaufman | 75/212 |
| 4,060,414 | 11/1977 | Kaufman | 75/246 |
| 4,092,223 | 5/1978 | Kaufman | 204/23 |
| 4,309,457 | 1/1982 | Kawasumi et al. | 427/214 |
| 4,309,458 | 1/1982 | Kawasumi et al. | 427/217 |
| 4,661,071 | 4/1987 | Bell et al. | 433/223 |
| 4,742,861 | 5/1988 | Shoher et al. | 164/80 |
| 4,814,008 | 3/1989 | Shoher et al. | 75/252 |
| 4,855,101 | 8/1989 | Mohs et al. | 419/8 |
| 4,970,050 | 11/1990 | Groll et al. | 419/36 |
| 4,997,373 | 3/1991 | Tanaka et al. | 433/204 |
| 5,106,303 | 4/1992 | Odén et al. | 433/223 |
| 5,118,296 | 6/1992 | Eldred | 433/223 |

*Primary Examiner*—Donald P. Walsh
*Assistant Examiner*—Daniel J. Jenkins
*Attorney, Agent, or Firm*—Stevens, Davis, Miller & Mosher

[57] ABSTRACT

This invention relates to a powder substantially of dental metal, which powder is suitable for the manufacture of a dental restoration such as a crown or a bridge, comprising a substructure of dental metal and a fired on coating of a dental ceramic material. The powder comprises a core substantially of a dental metal, which core is coated with one or more layers substantially of metal which protect the dental metal of the core during sintering against oxidation and/or reduce the temperature at which the powder is sintered.

The invention also relates to a process for the manufacture of a dental restoration such as a crown or a bridge, comprising a substructure of a dental metal and a fired on coating of a dental ceramic material. This process comprises mixing a powder substantially of dental metal into a paste-like slurry, placing on a refractory model the resulting paste in the form of the restoration to be made, heating the composite thus obtained to a temperature sufficient to sinter the powder of dental metal to a massive metal mass, and firing on a coating of a dental ceramic material on the substructure thus obtained, optionally after finishing the surface. As powder of dental metal the powder according to the invention is used.

2 Claims, No Drawings

POWDER OF DENTAL METAL, A PROCESS FOR THE PREPARATION THEREOF, A PROCESS FOR THE MANUFACTURE OF A SUBSTRUCTURE FOR A DENTAL RESTORATION AND A PROCESS FOR THE MANUFACTURE OF A DENTAL RESTORATION

This is a division of application Ser. No. 07/660,020 filed Feb. 25, 1991, now U.S. Pat. No. 5,238,751.

This invention relates to a powder substantially of dental metal, which powder is suitable for the manufacture of a dental restoration such as a crown or a bridge, comprising a substructure of dental metal and a fired on coating of a dental ceramic material. The invention also relates to a process for the preparation of such a powder of dental metal.

Furthermore, the invention relates to a process for the manufacture of a dental restoration such as a crown or a bridge, comprising a substructure of a dental metal and a fired on coating of a dental ceramic material, which process comprises mixing a powder substantially of dental metal into a paste-like slurry, placing on a refractory model the resulting paste in the form of the restoration to be made, heating the composite thus obtained to a temperature sufficient to sinter the powder of dental metal to a massive metal mass, and firing on a coating of a dental ceramic material on the substructure thus obtained, optionally after finishing the surface.

The invention further relates to a process for the manufacture of a substructure for a dental restoration such as a crown or a bridge, comprising a substructure of a dental metal and a fired on coating of a dental ceramic material, which process comprises mixing a powder substantially of dental metal into a paste-like slurry, placing on a refractory model the resulting paste in the form of the restoration to be made, heating the composite thus obtained to a temperature sufficient to sinter the powder of dental metal to a massive metal mass and optionally finishing at the surface the substructure thus obtained.

Dental restorations of metal with a fired on coating of a ceramic material are still manufactured in practice by casting the selected dental alloy by the so-called "lost-wax process". By this known process the dental alloy in the molten state is poured into a refractory casting mold having the shape of the burned-out wax model.

The relative process comprises the following steps:
1. First the dentist takes an impression of the preparation in the mouth with a impression mass comprising substantially silicone material.
2. Then a positive casting of the impression in plaster is made from the model.
3. The dental mechanic models a wax model on the plaster model.
4. The wax model is provided with supply channels of wax and embedded in a refractory mass.
5. The mold of refractory material is heated to a temperature of 600°–1000° C.
6. Then the liquid metal is poured into the resulting cavity. Upon cooling, the casting undergoes heat shrinkage to be compensated by the refractory mass through expansion occurring when the mold is heated.
7. The cast articles are finished with ceramically bound stones or hard metal cutters and then coated, if desired, with a dental ceramic material (this term is used here in the extended meaning of ceramic material suitable for dental applications and particularly comprises dental porcelain).

In the literature, suggestions have already been made for less laborious methods for the manufacture of dental restorations (i.e. restorations of the teeth, e.g., in the form of a bridge, a crown, a plate, etc.), with the above steps 2 through 6 being replaced by the following three steps:

a. The impression is cast into a refractory material instead of plaster, and the model is burned out at a temperature of 1000°–1200° C.; the refractory material may consist of a mixture of quartz sand with a certain particle distribution and magnesium oxide and biammonium phosphate as binders; the powder is mixed with colloidal silica into a slurry; the slurry is poured into the impression and binds within 5–10 minutes to form a hard mass.

b. The metal in the form of a slurry is placed on the refractory model at the pertinent locations; the suitably produced metal powder is mixed with, e.g., propylene glycol, ethylene glycol or polyethylene glycol so as to obtain a spreadable mass of paste-like consistency. Instead of the glycols referred to, various other substances may be used, e.g., polyvinyl alcohol, high fusing waxes and celluloses such as methyl cellulose and carboxymethyl cellulose.

c. The powder applied is sintered to a massive metal mass at a temperature of 1000°–1300° C.

In order to avoid oxidation, this last step is carried out under vacuum, which, however, requires the use of a suitably developed furnace as disclosed in U.S. Pat. No. 4,702,696. In order to avoid the economic drawbacks connected with the use of such a special furnace, it has also been proposed to use only powders of precious metal. This, however, also entails considerable expense, while, furthermore, a stable oxide layer necessary for binding with porcelain is hard to form on alloys consisting only of precious metals.

U.S. Pat. No. 3,502,466 discloses a process for the manufacture of articles, especially dental crowns, using metal powders, particularly precious metal powders. The metal powder is first mixed with a binder to form a paste or putty. After the resulting paste has been molded into the desired shape, it is heated so that the binder escapes and the metal powder is sintered to a compact mass. Examples of metal powders disclosed in this publication are a powder of pure gold, a powder of a gold-platinum-palladium-silver alloy, a powdered mixture of gold, platinum, palladium, silver and silicon (or aluminum) and a powdered mixture of titanium and nickel.

Such a process is further disclosed in U.S. Pat. No. 4,661,071. This shows the use of a metal powder consisting of, e.g., a mixture of a nickel-chromium and a nickel-chromium-silicon alloy or of a nickel-boron-silicon alloy. The powder must be sintered at a reduced pressure of 10–1000 $\mu$m Hg, preferably at a pressure of 10–100 $\mu$m Hg, which, however, requires an expensive high-vacuum furnace.

German patent application 35 32 331 proposes for such a process to use a metal powder which is a mixture of at least a coarse fraction having a particle size preferably from 30 to 100 $\mu$m and a fine fraction having a particle size below about 50 $\mu$m. The powdered mixtures may be based on precious metals, but also alloys containing base metals may be used, such as a powder which is a mixture of a gold-tin-indium alloy with gold and platinum powder; in order to avoid oxidation of tin and indium during sintering, sintering is carried out under a graphite bell in a conventional porcelain furnace.

This known process has the additional drawback that owing to differences in particle size and specific mass of the constituent elements segregation can easily occur, resulting in an undesirable inhomogeneity of the final product (but physical properties thereof are not mentioned).

Under normal conditions of temperature and sintering time the production of sintered restorations from mixtures of elements may give rise to a chemically inhomogeneous product. Inferior mechanical properties result from such inhomogeneity in the microstructure of the material. Furthermore, the use of a powdered mixture leads to swelling during sintering, which may lead to cracks in the final product. If the rate of diffusion is not equal, this will result in pore formation and weakening of the sintered product.

All known processes using a powdered mixture of different metals or of different particle sizes will lead to a brittle product of low ductility. The elongation at break of an alloy is deemed decisive of the ductility. In case of using oxidizable alloys, low ductility may also be attributed to the formation of an oxide film on the powder particles so that no coherent homogeneous sintering product is formed.

U.S. Pat. No. 4,742,861 discloses a process for the manufacture of a dental restoration, which comprises using a metal powder which is a mixture of a major amount of a high fusing component such as platinum and palladium and a minor amount of a low melting component such as gold. By means of a binder such a mixture is mixed into a pasty mass. After this paste has been molded into the desired shape, it is heated to a temperature below the melting point of the high fusing component, at which, however, the low fusing component melts and forms a porous open structure together with the high fusing component. To this porous open structure a low fusing filler material, e.g. gold, is added to obtain a massive body after melting thereof.

A problem of the impregnation of low fusing material is that this component may seep from the restoration on all sides so that the restoration gets another outside dimension and no longer fits. A second drawback is that the metals give no stable oxide layer necessary for a proper adhesion to the procelain to be fired on.

According to U.S. Pat. No. 4,814,008 use is made of an aggregate of two different metal powders. A component constituting 1–15 vol. % of the mixture is composed of a powder of platinum or palladium having a particle size preferably 5–10 times larger than the second component consisting of a fine powder of e.g. gold. During sintering the mixture is converted into a massive metal.

As a result of the large amount (85–99 vol. %) of a low fusing precious metal this process leads to a semi-alloyed mass of low stability at the firing temperature required for the conventional porcelains. A second drawback is that on the metal structure the metals used do not form a stable oxidation layer required to obtain chemical bonding between metal and porcelain.

The present invention has for its object to remove the drawbacks of these known methods and realizes this object by means of a powder substantially of dental metal, which powder is suitable for manufacture of a dental restoration such as a crown or a bridge, comprising a substructure of dental metal and a fired on coating of a dental ceramic material, which powder is characterized according to the invention in that the powder comprises a core substantially of a dental metal, which core is coated with one or more layers substantially of metal which protect the dental metal of the core during sintering against oxidation and/or reduce the temperature at which the powder is sintered.

This invention also relates to a process for the manufacture of a dental restoration such as a crown or a bridge, comprising a substructure of a dental metal and a fired on coating of a dental ceramic material, which process comprises mixing a powder substantially of dental metal to form a paste-like slurry, placing on a refractory model the resulting paste in the form of the restoration to be made, heating the resulting composite to a temperature sufficient to sinter the powder of dental metal to a massive metal mass and to fire on a coating of dental ceramic material on the substructure thus obtained, if required after finishing the surface, and to a process for the manufacture of a substructure for a dental restoration such as a crown or a bridge, comprising a substructure of a dental metal and a fired on coating of a dental ceramic material, which process comprises mixing a powder substantially of dental metal to form a paste-like slurry, placing on a refractory model the resulting paste in the form of the restoration to be made, heating the resulting composite to a temperature sufficient to sinter the powder of dental metal to a massive metal mass and, if required, finishing the resulting substructure at the surface, which processes are characterized by using as powder of dental metal a powder according to the invention.

The powder according to the invention comprises a core of dental metal, which core is provided with a one or multiple layered coating, it being preferred that the one or multiple metal layered coating of the core consisting of dental metal comprises at least one layer of either (a) a metal having a lower melting point than the dental metal of the core or (b) a metal capable of reacting with the dental metal of the core or with a metal from an adjacent coating layer to form a material having a lower melting point than the dental metal of the core.

A specifically preferred embodiment of the powder according to the invention is characterized in that the one or multiple metal layered coating of the core consisting of dental metal comprises at least one layer of a precious metal or of a non-oxidizing precious metal alloy.

More in particular, it is preferred that the one or multiple metal layered coating of the core consisting of dental metal comprises at least one layer of gold, palladium, platinum, iridium, rhodium or ruthenium.

Certain preferred embodiments of the invention are characterized in that the one or multiple metal layered coating of the core consisting of dental metal comprises at least one inside layer of copper, nickel, indium, tin, gallium or zinc and at least one outside layer of gold, palladium, platinum, iridium, rhodium or ruthenium.

A very specifically preferred embodiment of the invention is characterized in that the one or multiple metal layered coating of the core consisting of dental metal comprises at least one inside layer of palladium and at least one outside layer of gold.

All dental alloys developed for the porcelain-metal technique in the course of times may be used for the core of the powder. Dental alloys proposed for firing on a ceramic material may be subdivided into the following four groups:

1) Pt-Au alloys, e.g., 85% Au, 8% Pt, 5% Pd, 2% In.
2) Pd-Au alloys, e.g., 52% Au, 38% Pd, 8% In, 2% Ga.
3) high-Pd alloys, e.g., 79% Pd, 2% Au, 10% Cu, 9% Ga.
4) Ag-Pd alloys, e.g., 54% Pd, 38% Ag, 8% Sn.

These alloys have been found satisfactory in clinical conditions and have very favorable biological properties as a result of their composition. After many years of progressive development they have reached a high level which is particularly expressed by the fact that only few problems occur with respect to porcelain-metal bonding, porcelain cracks, polishing and behavior in the mouth.

In addition, the invention creates new possibilities such as the use of alloys or metals that are hardly pourable, if pourable at all, such as pure titanium. Titanium has been found to be a biologically very favorable metal, especially in implantates; no allergic reactions with patients are known. Since titanium is an extremely reactive metal having a high affinity for oxygen, titanium cannot be cast by the known methods according to the lost-wax process. Only with greatest effort can a titanium casting of reasonable quality be obtained under a very high vacuum (pressure below 0.01 mbar). Partly owing to the high melting point and the high reactivity of titanium, it is hard to find a refractory material satisfying all requirements in which the metal can be cast without reacting therewith. Up to now, attempts to make a completely homogenous titanium casting without the presence of oxide inclusions and porosity have not been successful. However, the idea according to the invention of a coated dental metal powder now renders it possible to make dental restorations from titanium. Thus, according to the invention an internal oxidation of the titanium at temperatures about 600° C. can be inhibited by applying a layer of platinum or palladium forming a barrier to penetration of oxygen.

According to the invention it is preferred that the dental metal of the core consists of a platinum-gold dental alloy, a palladium-gold dental alloy, a high-palladium dental alloy, a silver-palladium dental alloy or of titanium metal.

Specifically preferred according to the invention is a powder which is characterized in that the core consists of a platinum-gold dental alloy, a palladium-gold dental alloy, a high-palladium dental alloy or a silver-palladium dental alloy, which core is successively coated with a layer of palladium and a layer of gold.

Another specifically preferred embodiment of the invention is characterized in that the core consists of titanium metal and the core is successively coated with a layer of copper or nickel, a layer of palladium and, if required, a layer of gold.

The powder according to the invention will normally have a particle size of not more than 100 $\mu$m, preferably not more than 75 $\mu$m. In the powder according to the invention the one or multiple layered coating of the core will normally have a thickness of 1-75 $\mu$m, preferably 5-65 $\mu$m. The one or multiple layered coating of the core will normally constitute 1-50 vol. %, preferably 5-25 vol. % of the powder.

As a result of its proper distribution over the entire powder, the added coating has no negative effect on the homogeneity, decrease the risk of forming undesirable oxides and leads to accelerated sintering resulting from the fact that a lower fusing material is present or is formed at the surface of the particles. The applied one or multiple layered dense coating makes it no longer necessary to sinter under high vacuum, and sintering may be conducted by means of a normal porcelain furnace, which is an important economical advantage over the processes requiring the use of special equipment.

The method of preparing the powder according to the invention is not critical per se. Layers consisting of a pure metal or a metal alloy may be applied, e.g., both by a galvanic (electrolytic) process and by high-vacuum sputtering (cathode sputtering) techniques.

Preferred is a process in which the one or multiple metal layered coating of the core is applied by an electrolytic process. According to a suitable preferred embodiment, the powder to be coated is stirred continuously by means of a stirrer connected as cathode, the powder being in contact with an electrolyte containing a compound of the metal to be deposited on the powder. In order to optimally avoid excessive metal deposition on the stirrer, the stirrer is preferably provided in the part passing through the electrolyte with an insulating jacket or coating. The anode is preferably enclosed with a membrane preventing contact between the powder and the anode.

The words "powder substantially of dental metal", as occasionally used in the claims, comprise embodiments in which the powder contains admixtures, i.e. consists of a powdered mixture. For the purpose of, e.g., influencing the sintering behavior, such admixtures may consist of metallic, oxidic or ceramic materials such as, e.g., boron, silicon, pulverized dental porcelain, yttrium oxide, boron oxide, silica, etc. Boron and silicon powder may function, e.g., as an additional deoxidizer during sintering and form low fusing eutectics with the outer layer of the metal powder. Dental porcelain powder may serve to fill remaining pores and to promote moistening of the refractory branch material. For this purpose, e.g. yttrium oxide and boron oxide may also be used.

There are no restrictions with regard to the amount of such possible admixtures. In general, these will be admixtures in amounts up to about 10 wt. %, preferably not more than 5 wt. %.

The invention will be further illustrated with reference to some practical examples which are provided herein for purpose of illustration only and are not intended to be limitative of the scope of the invention.

EXAMPLE I

A frequently used dental alloy having the following composition: 81% palladium, 10% copper and 9% gallium was atomized to a very fine powder in a so-called inert gas atomizer. The metal powder was sieved at 45 $\mu$m to remove the coarse portion.

The powder was placed as a layer of about 2 cm on the bottom of a 200 ml beaker used for application of a metal coating by electrolysis. The cathode consisted of a rod of stainless steel bent to an L shape and having a diameter of 4 mm. The vertical part of the "L" was covered by an insulating coating film. The horizontal part of the "L" was completely covered by the powder layer. In order to avoid that the powder particles could lose their negative charge owing to collision with the anode, the anode was enclosed with a membrane of glass wool which stopped the powder particles indeed, but ensured a proper galvanic passage of ions.

The solution consisted of:

| | |
|---|---|
| Pd (as palladium chloride) | 50 g/l |
| hydrochloric acid | 60 ml/l |
| ammonium chloride | 30 g/l |
| current density (anode) | 1.0 A/dm$^2$ |
| temperature | 40° C. |

The potential difference over the galvanic cell was from 0.5 to 1.0 V. After some time a compact and dense layer of palladium was formed on the powder, which layer was not cracked even in the case of larger thicknesses.

The powder was washed with distilled water and again placed in the beaker. To the powder were added 100 mL gold cyanide liquid consisting of

| | |
|---|---|
| Au (as gold cyanide) | 30 g/l |
| potassium cyanide | 100 g/l |

A potential difference of about 1 V was applied over the cell, the cathode being reciprocated in the powder carefully but continuously. After 30 minutes the powder was separated by filtration of the liquid, then washed and dried. A gold layer of 10 µm deposited on the powder. This represented a gold content of 8 wt. % on the total alloy.

Of the powder, strips of 12×3×1 mm were sintered in a refractory model. These were tested for bending strength in a three-point bending test with a supported length of 9 mm. The untreated powder gave values for the tensile break ranging from 100 to 200N, the coated powder giving a value of 800N.

A strip produced by the above method was oxidized for 10 minutes at 950° C. A dark grey stable oxide layer was formed. The strip was bent around a metal shaft of 10 mm diameter, with most of the ceramic material separating from the alloy. Inspection of the area of fracture showed that half of it was covered with porcelain residues, which indicates that the fracture occurred mainly in the porcelain itself so that the adhesion was satisfactory.

EXAMPLE II

An atomized powder of pure titanium having a particle size of 90% smaller than 45 µm was used as starting material. The titanium powder was first washed in a solution of tin (II) chloride and then washed in a copper sulfate solution to apply a thin copper layer.

By an electrolytic process a palladium layer was applied from a solution having the composition:

| | |
|---|---|
| Pd (as palladium chloride) | 50 g/l |
| hydrochloric acid | 60 ml/l |
| ammonium chloride | 30 g/l |
| current density (anode) | 1.0 A/dm$^2$ |
| temperature | 40° C. |

The potential difference over the galvanic cell was from 0.5 to 1.0 V. After some time a compact and dense layer of palladium was formed on the powder, which layer was not cracked even in the case of larger thicknesses.

After a layer of about 50 µm had been deposited on the metal powder, the powder was separated from the solution by filtration. After washing thoroughly in distilled water the powder was dried. It was mixed by means of polyethylene glycol to form a creamy consistency and placed on a refractory model. Then the powder was sintered to a solid body at 1100° C. in a standard porcelain furnace.

An optical study with a microscope showed no appreciable porosity in the metal. The galvanic coating of palladium was diffused entirely into the titanium. The alloy gave the normal metallic structure of pure titanium, but without the inhomogeneities as those occurring with cast titanium.

The three-point bending test gave a value of 420N instead of 50N after sintering of uncoated titanium powder. A strip of the titanium obtained by the above process was fired on with a commercial porcelain for titanium in two layers, namely an opaque layer having a thickness of 0.2 mm and a dentine layer having a thickness of 0.8 mm. The strip was then bent around a metal shaft having a diameter of 10 mm, with most of the ceramic material separating from the alloy. Inspection of the area of fracture showed that half of it was covered with porcelain residues, which indicates that the fracture occurred mainly in the porcelain itself so that the adhesion was satisfactory.

What I claim is:

1. A process for the manufacture of a dental restoration such as a crown or a bridge, having a substructure of a dental metal and a fired on coating of a dental ceramic material, comprising mixing substantially into a paste-like slurry, a powder comprising a core substantially of a dental metal, which core is coated with at least one layer substantially of metal which protects the dental metal of the core during sintering against oxidation and/or reduces the temperature at which the powder is sintered, placing the resulting paste-like slurry on a refractory model in the form of the restoration to be made, heating the composite thus obtained to a temperature sufficient to sinter the powder of dental metal to a massive metal mass and form a substructure and firing on a coating of a ceramic material on the substructure to form the dental restoration.

2. The process according to claim 1 including finishing the surface of the substructure prior to firing on the coating of the dental ceramic.

* * * * *